(12) United States Patent
Basset et al.

(10) Patent No.: US 6,590,084 B2
(45) Date of Patent: Jul. 8, 2003

(54) PROCESS FOR PREPARING AND ISOLATING 9-DEOXO-9 (Z)-HYDROXYIMINOERYTHROMYCIN A

(75) Inventors: François Basset, Villeurbanne (FR); Thierry Durand, Ecully (FR); Ronan Guevel, Lyons (FR); Patrick Leon, Tassin la Demi-Lune (FR); Frédéric Lhermitte, Saint Symphorien d'Ozon (FR); Gilles Oddon, Lyons (FR); Denis Pauze, Solaize (FR)

(73) Assignee: Merial, Lyons (FR)

( * ) Notice: Subject to any disclaimer, the term of this patent is extended or adjusted under 35 U.S.C. 154(b) by 79 days.

(21) Appl. No.: 09/740,671

(22) Filed: Apr. 23, 2001

(65) Prior Publication Data

US 2001/0034434 A1 Oct. 25, 2001

Related U.S. Application Data

(60) Provisional application No. 60/186,129, filed on Mar. 1, 2000.

(30) Foreign Application Priority Data

Dec. 20, 1999 (FR) ............................................. 99 16106

(51) Int. Cl.[7] .............................. C07H 17/08; C07H 1/00
(52) U.S. Cl. ...................................... 536/7.4; 536/18.5
(58) Field of Search ................................. 536/7.5, 18.5

(56) References Cited

U.S. PATENT DOCUMENTS

| 5,635,613 A | * | 6/1997 | Greene et al. | ............. 536/18.5 |
| 5,808,017 A |   | 9/1998 | Chang |   |
| 5,912,331 A | * | 6/1999 | Wilkening | ................... 536/7.4 |

FOREIGN PATENT DOCUMENTS

| EP | 0 503 932 A1 | 9/1992 |
| EP | 0 503 949 A1 | 9/1992 |
| EP | 0 508 699 A1 | 10/1992 |

* cited by examiner

*Primary Examiner*—Elli Peselev
(74) *Attorney, Agent, or Firm*—Frommer Lawrence & Haug LLP; William S. Frommer; Thomas J. Kowalski

(57) ABSTRACT

The present invention relates to a process for preparing 9-deoxo-9(Z)-hydroxyiminoerythromycin A corresponding to formula (I) below:

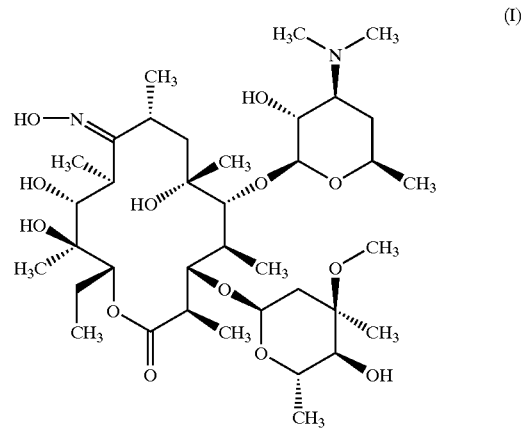

from 9-deoxo-9(E)-hydroxyiminoerythromycin A by reaction with a base in water or in a mixture of water/solvent of dialkyl ketone type capable of forming a crystallizable solvate with the desired 9(Z)-oxime; acidification of the reaction mixture to a pH of between 9 and 11; addition to the said mixture of an organic solvent; optionally concentration under vacuum of the resulting organic phase; and isolation of the desired 9(Z)-erythromycin oxime.

22 Claims, No Drawings

PROCESS FOR PREPARING AND ISOLATING 9-DEOXO-9 (Z)-HYDROXYIMINOERYTHROMYCIN A

This application claims priority of pending U.S. Provisional application Serial No. 60/186,129, filed Mar. 1, 2000.

The present-invention-relates to a process for preparing and isolating 9-deoxo-9(Z)-hydroxyimino-erythromycin A (referred to hereinbelow as 9(Z)-erythromycin oxime or 9(Z)-oxime) from the corresponding E isomer.

The present invention lies in the field of macrolide antibiotics of erythromycin type and relates more particularly to their aza-macrolide derivatives which are the subject of patent application EP 508 699 and correspond to the following general formula:

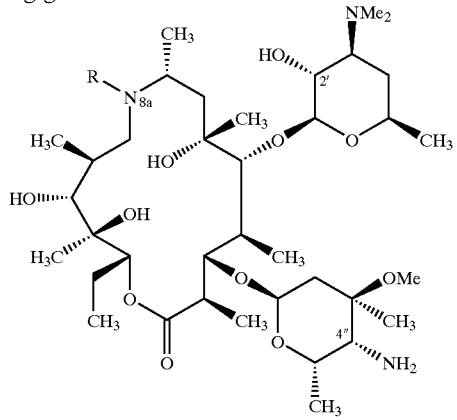

in which R represents a hydrogen atom, a $C_1$–$C_{10}$ alkyl group, a $C_2$–$C_{10}$ alkenyl group or a $C_6$–$C_{12}$ arylsulphonyl group, which may be substituted.

These compounds are obtained from erythromycin and their synthesis involves two major steps:
- the creation of the 8a-azalide macrocycle from 9(E)-erythromycin oxime isomerized into the corresponding 9(Z)-oxime, which then undergoes a stereospecific Beckmann rearrangement, and
- the modification of the "cladinose" group in position 4, which consists in converting the 4(S)-OH into 4(R) -$NH_2$.

The present invention relates more particularly to the first step of this synthesis and its subject is a new process for isomerizing 9(E)-erythromycin oxime and isolating the resulting 9(Z)-oxime isomer, which can be illustrated as follows:

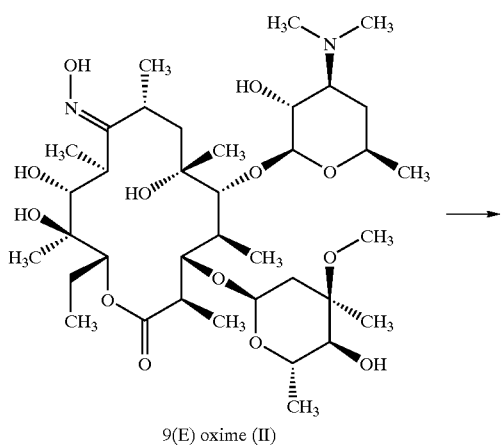

9(E) oxime (II)

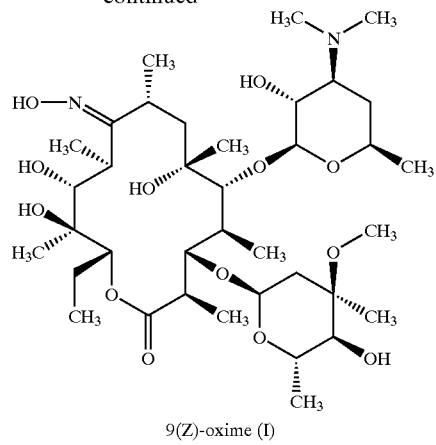

9(Z)-oxime (I)

This isomerization step is, in particular, the subject of patent application EP 503 949, in which the 9(Z)-oxime of formula (I) is obtained by treating the E isomer of formula (II) with a base, preferably an alkali metal hydroxide such as lithium hydroxide, in a protic or aprotic solvent which is preferably ethanol. The residue obtained after evaporating off the solvent is taken up in ethyl acetate and an aqueous solution which is then re-extracted with ethyl acetate to give a crude product containing a mixture of oximes. The crude mixture of oximes is then taken up in methylene chloride, then filtered. The solid obtained is then taken up in ethyl acetate and a non-solvent (nitromethane) and then crystallized or purified in ethyl acetate by successive steps of precipitation with methylene chloride, and filtrations.

As it turns out, the current conditions cannot be extrapolated to the industrial scale.

The reason for this is that this process involves steps of concentrating to dryness of the reaction mass in ethanol and of that in ethyl acetate.

It also involves the use of chlorinated solvents that are undesirable in terms of environmental protection.

Finally, the product isolated still contains the (E) isomer and needs to be taken up several times in a medium containing ethyl acetate and methylene chloride in order to crystallize (by "beating") the desired (Z) isomer and to isolate it in an acceptable isomeric purity.

The aim of the present invention is to provide an efficient alternative to the known process which makes it possible to overcome the abovementioned drawbacks.

The aim of the invention is thus to provide a simplified process, which is easy to carry out on the industrial scale and which gives the 9(Z)-oxime in a satisfactory isomeric purity.

The aim of the invention is, in particular, to avoid the use of chlorinated solvents, that are environmentally harmful, as well as the laborious purification by "beating" in an ethyl acetate/methylene chloride mixture.

A subject of the present invention is a process for preparing 9-deoxo-9(Z)-hydroxyiminoerythromycin A corresponding to formula (I) below:

(I)

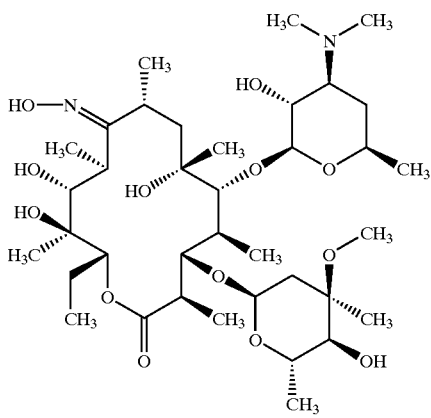

successively comprising the steps consisting in:
reacting in water 9-deoxo-9(E)-hydroxyimino-erythromycin A corresponding to formula (II) below:

(II)

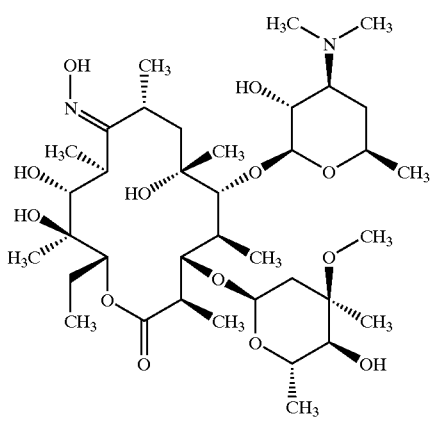

with a base,
acidifying the reaction mixture to a pH of between 9 and 11,
adding to the said mixture an organic solvent;
optionally concentrating under vacuum the resulting organic phase;
isolating the desired 9(Z)-erythromycin oxime.

According to a preferred variant of the invention, for the reaction of the 9(E)-oxime of formula (II), an organic solvent of dialkyl ketone type, in particular acetone, is added to the water.

The inventors have demonstrated, unexpectedly, that 9(E)-erythromycin oxime suspended in water, optionally with the addition of a solvent of the dialkyl ketone type, can be isomerized with a base, without the presence of an alcoholic solvent, followed by directly extracting, after neutralization of the salt, the desired isomer from the reaction suspension and isolating it in a satisfactory purity.

They have thus demonstrated that the desired (Z) isomer can be obtained by adding to the reaction suspension an organic solvent such as ethyl acetate allowing it to be crystallized without addition of another solvent to the medium. Depending on the case, this medium may be capable of forming an insoluble or sparingly soluble solvate with the 9(Z)-oxime. It does not require any subsequent crystallizations.

According to one embodiment, the invention thus covers the use, after isomerization in water, of any organic solvent capable of inducing the crystallization of the 9(Z)-oxime, in particular by concentration, in the said solvent, while the (E) isomer remains mainly dissolved in the medium.

According to a preferred variant, it is the actual isomerization which is carried out in water to which is added an organic solvent of dialkyl ketone type capable of forming a crystallizable solvate with the (Z) isomer as indicated above.

The inventors have thus developed a simplified process for dispensing with the precipitation with methylene chloride as well as the multi-step purification required in the known process.

The inventors have also demonstrated that the mother liquors (containing a mixture of the E and Z isomers) collected after isolation of the crystallized (Z) isomer can advantageously be recycled by reforming an aqueous suspension of the mixture of isomers they contain after removal of most of the organic solvent present.

The process according to the invention will be described in greater detail below.

This process consists firstly in treating 9(E)-erythromycin oxime, suspended in water, with a base which is preferably water-soluble.

According to a preferred variant of the invention, the 9(E)-oxime is reacted with the base, in an aqueous medium formed of water mixed with an organic solvent of dialkyl ketone type and advantageously capable of forming a crystallizable solvate with the 9(Z)-oxime, while the (E) isomer remains mainly in solution. The solvent of dialkyl ketone type is preferentially chosen from dialkyl ketones containing from 3 to 10 carbon atoms and it is typically acetone.

The base is then added to give rise to the isomerization reaction. Examples of bases which may be mentioned are alkali metal or alkaline-earth metal hydroxides, ammoniums, carbonates and alkoxides. This base preferably consists of lithium hydroxide or sodium hydroxide.

The base is used in an amount preferably of between 1 and 10 equivalents, preferably 2 molar equivalents relative to the 9(E)-oxime.

The addition of the base to the 9(E)-oxime leads to its deprotonation and makes it possible to reach the equilibrium conditions with the (Z) isomer.

The pH of the reaction medium is generally between 11.5 and 14.

The subsequent treatment applied to the mixture makes it possible to shift this equilibrium and preferentially to isolate the 9(Z)-oxime in the form of solvate.

The reaction is generally carried out under an inert atmosphere. The Z/E ratio is temperature-dependent and the reaction is preferably carried out at a temperature of between 10° and 25° C., more preferably in the region of 20° C.

The reaction medium is preferably stirred for 6 to 24 hours.

The desired (Z) isomer is then extracted with an organic solvent, in particular with ethyl acetate or another equivalent solvent.

To do this, the reaction mixture is first acidified to a pH preferably of between 9 and 11, even more preferably to a pH of about 9.5–10. For this, hydrochloric acid, acetic acid or sodium bicarbonate is preferably used.

To carry out this acidification step, the said mixture is preferably cooled to a temperature below 20° C., and more preferably to a temperature of about An organic solvent is then added to the reaction medium in order to induce the crystallization of the desired (Z) isomer.

When the isomerization reaction is conducted in water, according to one preferred embodiment of the invention, ethyl acetate or other solvents which have equivalent properties in terms of crystallization of the (Z) isomer is used.

The expression "solvents which have equivalent properties of crystallizing the (Z) isomer" means any solvent capable of inducing crystallization of the 9(Z)-oxime, in particular by concentrating the organic extraction phase, while the (E) isomer remains mainly in solution.

Specifically, according to this embodiment of the invention, it is thought that the (Z) isomer can be extracted directly from the reaction medium and can crystallize by concentration in the organic extraction solvent. When the isomerization reaction is carried out in a water/dialkyl ketone mixture, it is the solvate of the (Z) oxime with the dialkyl ketone which precipitates at the end of neutralization. The use of an organic solvent such as ethyl acetate or methyl butyl ether makes it possible to improve the Z/E ratio in favour of the desired (Z) isomer, during the filtration of the solvate with the dialkyl ketone. Moreover, an ester such as ethyl acetate also makes it possible to improve the subsequent drying of the (Z) oxime by promoting the removal of the solvent of dialkyl ketone type.

During the extraction step, the temperature of the reaction medium is preferably returned to room temperature (about 25–30° C.) which facilitates the separation of the phases by settling.

After separation of the phases by settling, the aqueous phase is preferably re-extracted under the abovementioned conditions.

Where appropriate, the organic extraction phases are combined and then concentrated under vacuum in order to bring about crystallization of the desired (Z) isomer in the medium.

The temperature of the reaction medium is preferably maintained below 35° C. during this concentration operation and is preferably carried out for several hours (for about 4 to 5 hours).

The desired (Z) isomer is then isolated by filtration. For this, the reaction mass is preferably maintained between 10 and 25° C., preferably cooled to a temperature of about 10° C.

The (Z) isomer is recovered in a Z/E ratio of greater than 90/10, typically between 93/7 and 98/2.

According to the invention, the mother liquors collected after filtration, which essentially contain the 9(E)-oxime, can be reprocessed as indicated above.

In this case, most of the ethyl acetate or other extraction solvent is distilled off under vacuum on a tail of water, until only 3 to 4% remains, for example.

A solvent of dialkyl ketone type and base are then added, if appropriate, as indicated above, in order to carry out a new isomerization of the 9(E)-oxime present, followed by isolation of the 9(Z)-oxime formed under the conditions indicated above.

Depending on the extraction solvent, a larger amount of base may need to be introduced on account of a possible saponification of the solvent.

The process according to the present invention has the advantage of using only one extraction solvent, which is generally not a chlorinated solvent, and of not requiring multiple repeats in order to obtain the crystallization of the desired isomer. It can be carried out easily in industrial terms.

The process according to the invention is illustrated below by examples which should not be considered as limiting.

EXAMPLE 1

Isomerization Reaction in Water

9(E)-Erythromycin oxime (II) (50 g, 0.065 mol, 1 equiv.) and lithium hydroxide LiOH·H$_2$O (5.7 g, 0.133 mol) are placed in a 1 liter homothetic reactor with a nitrogen atmosphere and distilled water (500 ml) is then added, while carefully rinsing out the conical flask used for adding the solids.

The 9(E)-erythromycin oxime suspension thus obtained is stirred for 9 hours or more at a temperature of about 16° C. (or at room temperature). The set temperature is then cooled to about 10° C. and 1N HCl solution is added over 1 h 30 min or more so as to bring the pH of the reaction mass to a value of about 9.5.

The suspension thus obtained is extracted with ethyl acetate (300 g). To improve the extraction, the reaction mass is heated to about 25–30° C. After separation of the phases by settling, the aqueous phase is back-extracted with ethyl acetate (2×225 g). The combined organic phases are then concentrated under vacuum by partial distillation of the ethyl acetate and the reaction mass is then cooled to about 10° C. for about 1 h 30 min and then filtered.

After filtration and drying, 32 g of 9(Z)-erythromycin oxime (I) are isolated (Z:E ratio=96:4 by $^1$H NMR). The mother liquors isolated (97 g) can be recycled as described in Example 2.

EXAMPLE 2

Recycling of the Mother Liquors

The filtration mother liquors (97 g) are placed in a 1 liter homothetic reactor under a nitrogen atmosphere and distilled water (500 ml) is then added. The ethyl acetate is distilled off under vacuum until only about 3 to 4% by weight of ethyl acetate remains. Lithium hydroxide LiOH·H$_2$O (4.7 g, 0.109 mol) is then loaded in.

The suspension of the mixture of Z and E erythromycin oximes thus obtained is stirred at about 800 rpm for 10 hours or more at a temperature of about 16° C. (or at room temperature). The set temperature is then cooled to about 10° C. and 1N HCl solution is added over 1 h 30 min or more so as to bring the pH of the reaction mass to a value of about 9.5. Ethyl acetate (300 g) is then added and the mass is then heated to about 25–30° C. After separation of the phases by settling, the aqueous phase is back-extracted with ethyl acetate (2×225 g). The organic phase is rapidly transferred into the reactor and then concentrated under vacuum by partial distillation of the ethyl acetate down to a minimum stirrable volume. The reaction mass obtained is then cooled to about 10° C. for about 1 h 30 min and then filtered.

After filtration and drying, 6 g of 9(Z)-erythromycin oxime (I) are isolated (Z:E ratio≧96:4 by $^1$H NMR).

Weight yield=76%

EXAMPLE 3

Isomerization Reaction in a Water/Acetone Mixture

9(E)-erythromycin oxime A (115 g, 0.150 mol, 1 eq.) is loaded into a 1-liter reactor placed under an inert atmosphere of nitrogen, followed by addition of drinking water (220 g) and acetone (272 g), rinsing the funnel carefully. The suspension thus obtained is treated with 30% sodium hydroxide (38 g; 1.9 eq.) and then stirred for 8 hours or more at room temperature. The solution is then neutralized by addition of acetic acid over about 1 hour or more so as to bring the pH of the reaction mass to a value of about 10.

At this stage, a solvate is formed of the erythromycin oximes with the acetone (molar ratio 1:1 by $^1$H-NMR) which precipitates in the reaction medium.

The suspension thus obtained is treated with ethyl acetate (200 g) and then stirred for a minimum of 3 hours at room temperature, after which it is cooled to about 0° C. After stirring for about 3 hours at 0° C., the suspension is filtered and then washed with drinking water (360 g).

The product obtained is then taken up in-ethyl acetate (173 g) at about 40° C. and stirred at this temperature for about 3 hours. The suspension obtained is cooled to room temperature and then filtered.

After filtration and drying at 50° C., 78 g of 9-(Z)-erythromycin oxime are isolated (Z:E ratio≧97:3 by HPLC).

The data (distance and relative intensity) obtained by X-ray analysis of the 9(Z)-oxime (I) in the form of a solvate with acetone are given below:

| d (hkl) Å | Intensity (%) |
|---|---|
| 13.12 | 27 |
| 11.86 | 23 |
| 11.69 | 26 |
| 11.31 | 46 |
| 10.05 | 30 |
| 9.78 | 67 |
| 9.02 | 33 |
| 8.79 | 63 |
| 8.04 | 100 |
| 7.44 | 26 |
| 7.38 | 31 |
| 7.09 | 29 |
| 7.03 | 35 |
| 6.79 | 25 |
| 6.59 | 26 |
| 6.54 | 30 |
| 5.97 | 43 |
| 5.63 | 26 |
| 5.59 | 24 |
| 5.23 | 17 |
| 5.01 | 25 |
| 4.93 | 49 |
| 4.87 | 31 |
| 4.75 | 25 |
| 4.58 | 36 |
| 4.26 | 18 |
| 4.14 | 25 |
| 3.90 | 10 |
| 3.75 | 12 |
| 3.68 | 11 |
| 3.35 | 8 |
| 3.17 | 7 |
| 3.10 | 5 |
| 2.98 | 6 |
| 2.71 | 5 |
| 2.42 | 5 |

What is claimed is:

1. A process for preparing 9-deoxo-9(Z)-hydroxyiminoerythromycin A of the formula (1):

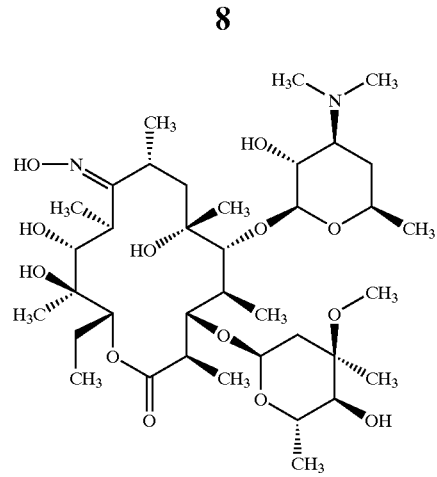

consisting essentially of:
a) reacting 9-deoxo-9(E)-hydroxyiminoerythromycin A of the formula (II):

in water and optionally in the presence of a dialkyl ketone solvent, with a base to form a reaction mixture;
b) acidifying said reaction mixture to a pH of between 9 and 11;
c) adding an ester solvent to said reaction mixture, and
d) isolating said 9-deoxo-9(Z)-hydroxyiminoerythromycin A.

2. The process according to claim 1, wherein said dialkyl ketone solvent is present and has 3 to 10 carbon atoms.

3. The process according to claim 1, wherein said dialkyl ketone solvent is present and is acetone.

4. The process according to claim 1, wherein said base is water soluble.

5. The process according to claim 1, wherein said base is an alkali metal or alkaline-earth metal hydroxide, ammonium, carbonate or alkoxide.

6. The process according to claim 1, wherein said base is lithium hydroxide or sodium hydroxide.

7. The process according to claim 1, wherein 1 to 10 molar equivalents of base is used relative to said 9-deoxo-9(E)-hydroxyiminoerythromycin A.

8. The process according to claim 1, wherein 2 molar equivalents of base is used relative to said 9-deoxo-9(E)-hydroxyiminoerythromycin A.

9. The process according to claim 1, wherein said reacting of said 9-deoxo-9(E)-hydroxyiminoerythromycin A in said water and base is performed at a temperature of between 10 to 25° C.

10. The process according to claim 1, wherein said reacting of 9-deoxo-9(E)-hydroxyiminoerythromycin A in water and base is performed at a temperature of about 20° C.

11. The process according to claim 1, wherein said reaction mixture is acidified to a pH of about 9.5 to 10.

12. The process according to claim 1, wherein said acidifying step utilizes hydrochloric acid, acetic acid or sodium bicarbonate.

13. The process according to claim 1, wherein said acidifying step is performed at a temperature below 20° C.

14. The process according to claim 1, wherein said acidifying step is performed at about 10° C.

15. The process of claim 1, wherein said ester solvent is ethyl acetate.

16. The process of claim 15, wherein in said concentrating step, the temperature of the organic phase is maintained below 35° C.

17. The process according to claim 1, wherein the step of isolating consists essentially of removing the 9(Z)-erythromycin oxime from an organic phase by filtration, said process further consisting essentially of a recycling step, which consists essentially of collecting the filtrates (mother liquors) formed during the filtration; combining the filtrates; removing most of the organic solvent from the combined filtrates; adding water, optionally a dialkyl ketone solvent, and a base to the combined filtrates; and isolating additional 9(Z)-erythromycin oxide which forms therefrom.

18. The process of claim 1 wherein there is an organic phase from adding the ester solvent to the reaction mixture, and the process additionally consists essentially of concentrating the organic phase under vacuum prior to the isolating step.

19. The process of claim 1 wherein the dialkyl ketone solvent is present in the reacting step.

20. 9-deoxo-9(Z)-hydroxyiminoerythromycin A of the formula (I):

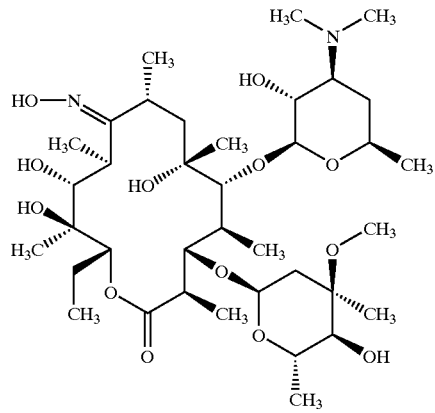

in the form of a solvate with a dialkyl ketone.

21. The 9deoxo-9(Z)-hydroxyiminoerythromycin A solvate of claim 20, wherein said dialkyl ketone has 3 to 10 carbon atoms.

22. The 9-deoxo-9(Z)-hydroxyiminoerythromycin A solvate of claim 20, wherein said dialkyl ketone is acetone.

* * * * *

UNITED STATES PATENT AND TRADEMARK OFFICE
CERTIFICATE OF CORRECTION

PATENT NO. : 6,590,084 B2 Page 1 of 1
DATED : July 8, 2003
INVENTOR(S) : Francois Basset et al.

It is certified that error appears in the above-identified patent and that said Letters Patent is hereby corrected as shown below:

<u>Title page,</u>
Item [75], Inventors, change "Lyons" to -- Lyon--
Item [73], Assignee, change "Lyons" to -- Lyon--

<u>Column 10,</u>
Line 25, change "9deoxo- 9(Z)-" to -- 9-deoxo-9(Z) --

Signed and Sealed this

Fourteenth Day of October, 2003

JAMES E. ROGAN
*Director of the United States Patent and Trademark Office*